United States Patent [19]
Comte

[11] Patent Number: 5,454,814
[45] Date of Patent: Oct. 3, 1995

[54] SURGICAL CLAMP AND CLAMP DRIVING DEVICE

[75] Inventor: Georges Comte, Monts de Vignes, France

[73] Assignee: Orthomed Sarl, France

[21] Appl. No.: 116,246

[22] Filed: Sep. 2, 1993

[30] Foreign Application Priority Data

Sep. 2, 1992 [FR] France .................................. 92 10722

[51] Int. Cl.[6] ............................................. A61B 17/68
[52] U.S. Cl. ............................................. 606/75; 606/219
[58] Field of Search ....................................... 606/151, 219, 606/220, 75, 72, 139, 142; 411/457–460, 473, 484, 920, 921, 923

[56] References Cited

U.S. PATENT DOCUMENTS 4,263,903  4/1981  Griggs .
4,454,875  6/1985  Pratt et al. .............................. 606/219
4,570,623  2/1986  Ellison et al. ............................ 606/75
4,723,540  2/1988  Gilmer, Jr. .............................. 606/75

FOREIGN PATENT DOCUMENTS 862764   9/1986  France .
2603794  3/1988  France .................................. 606/219

*Primary Examiner*—Tamara L. Graysay
*Attorney, Agent, or Firm*—Eckert Seamans Cherin & Mellott

[57] ABSTRACT

A surgical clamp is provided for insertion into a clamp driving device. The surgical clamp has two parallel anchoring legs linked by a common rectilinear section (1c) or yoke. The rectilinear section or yoke is suitable for being inserted into the driving device. The rectilinear section or yoke has a flat top, a bottom, and two edges. The two edges merge with the flat top by a generously rounded profile. On the one hand, the two edges merge with the bottom by an inclined flank at an obtuse angle with respect to the vertical plane. At least one of the insides of the legs, the outsides of the legs, and bottom of the yoke is serrated.

4 Claims, 3 Drawing Sheets

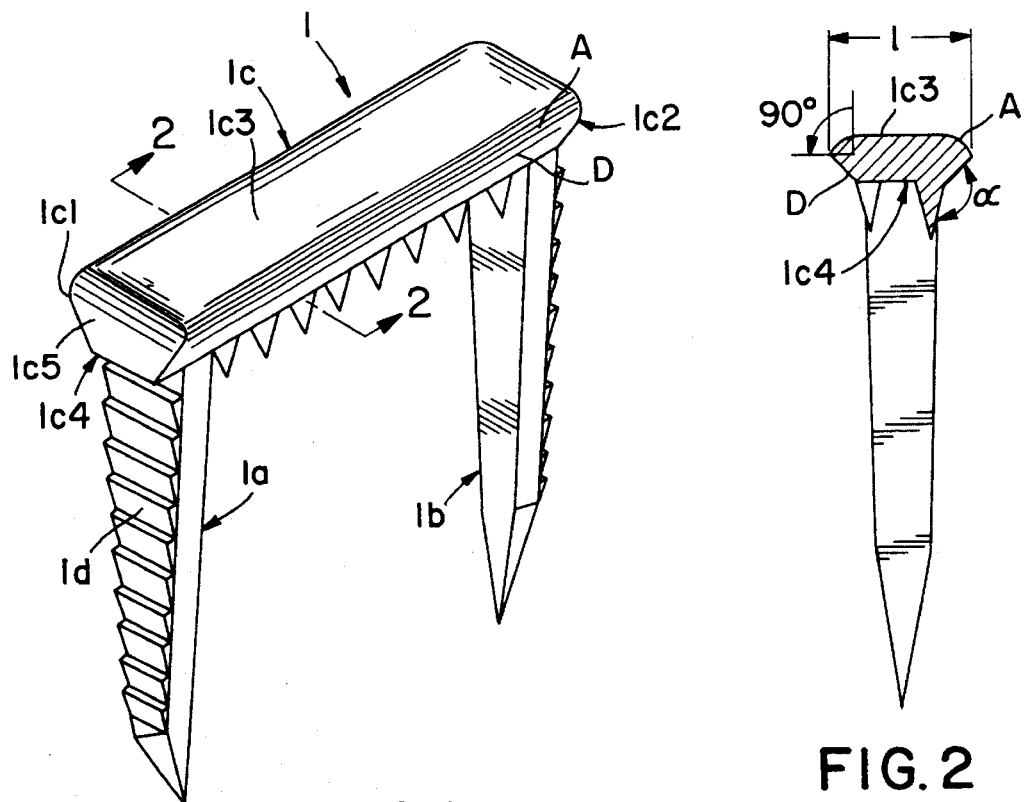
FIG. 1
FIG. 2
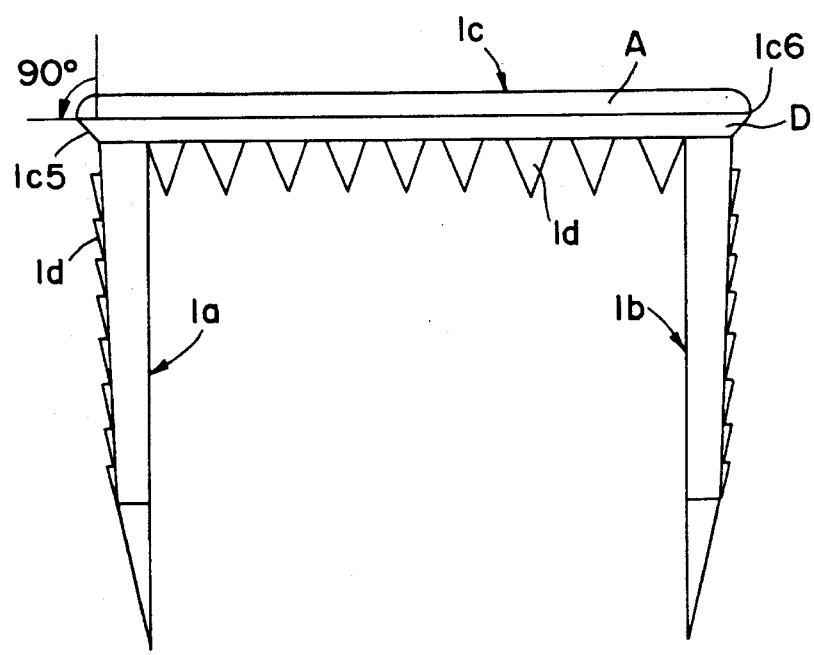
FIG. 3

SURGICAL CLAMP AND CLAMP DRIVING DEVICE

BACKGROUND OF THE INVENTION

1. Field of the Invention

The invention particularly relates to a surgical clamp of the type used in osteosynthesis and for the fixation of natural or artificial ligaments. The invention likewise relates to a device designed to drive and extract this clamp.

2. Prior Art

As is common knowledge among persons skilled in the art, surgical clamps comprise two parallel anchoring legs linked by a rectilinear part or yoke such that the clamp has the shape of an inverted-U. Leg tips are tapered into points to facilitate penetration.

Devices designed to position, drive and extract clamps for purposes of bone surgery are also know. The state of the art is illustrated by the specifications of U.S. Pat. No. 4,263,903, for instance. Basically, the clamp disclosed therein features a wedge-shaped yoke linking the legs and is designed to be inserted into the mating part of the driving device. The device features a moving part consisting of two jaws acting as pincers, said pincers being controlled by an actuator located at the end of a handle. The yoke of the surgical clamp dovetails into the jaws when the latter are closed.

Event though this solution is a satisfactory one as regards driving and extracting clamps, it appears that the wedge-shaped section of the latter comprises projecting parts that may cause tissue lesions. The drawback is the more significant when the clamp is flush with the skin. Lesions are quite frequent.

In an attempt to overcome such drawbacks, a clamp has been proposed the yoke of which, designed to be loaded into a clamp driving device, is free from asperities. The design is described in the specifications of patent FR 862764. The clamp concerned features a yoke with rounded edges on its upper half and a lower half tapering down to where the clamp legs start. The bottom of the yoke, therefore, is linked to the top by a large radius of curvature substantially representing a quadrant.

The driving device of the type described in U.S. Pat. No. 4,263,903, referred to above, features a moving part consisting of jaws acting as pincers, with the jaw insides mating the cross-section of the clamp yoke, the jaws notably featuring a large radius of curvature at their lips. The inherent risk of the design is a skewing motion of the clamp at the moment of impact, i.e., when the clamp is driven in. Indeed, the rounded edges of the yoke bottom combined with the rounded profile of the jaws gripping the yoke are unlikely to ensure a satisfactory angular hold.

SUMMARY OF THE INVENTION

The object of this invention is to solve the above problems in a simple, sure and effective manner.

The invention aims to solve two problems: firstly to ensure an angular lock on the surgical clamp and, secondly, to prevent impact lesions by designing a clamp yoke with no projecting parts at all.

To solve the problems, a clamp of the type featuring two parallel anchoring legs linked by a common rectilinear part or yoke was devised and developed for use with a driving device, characterized in that the yoke has a flat section and two of its edges at least are linked to the flat top by a generously rounded profile and to the bottom by a inclined flank at an obtuse angle with respect to the vertical plane.

To solve the problem of the asperities on the clamp top touching the skin, the rounded profile of the short edges of the yoke is constituted by an arc of a circle subtending substantially 90° at the center.

To solve the problem of the angular grip of the moving parts of the driving device, the inclined flanks are shaped directly in line with the rounded edges of the short ends of the yoke.

The transition area between the rounded edge of the short end and the inclined flank is advantageously located roughly in the middle of the height of the yoke.

To prevent the clamp from working loose, leg insides and/or outsides and/or the yoke bottom are serrated.

To solve the problem of perfectly mating the driving device to the clamp to preclude angular clamp motion at the moment of impact, the driving device of the type featuring a moving part consisting of two jaws acting as pincers controlled by an actuator located at the end of a handle is characterized in that each of the jaw insides is recessed to closely fit the cross-section of the yoke, locking the clamp in place at the moment it is driven into the part of the bone being secured.

A further problem this invention is intended to solve is that of driving the clamp totally home. The objective is achieved by designing curved jaw tips tapering inward, allowing the tips to be held in a position tangential to the surface of the bone at the point of impact so the clamp can be driven fully home, flush with the bone.

BRIEF DESCRIPTION OF THE DRAWINGS

In order that the present invention may more readily be understood, the following description is given, reference being made to the accompanying drawings in which:

FIG. 1 is a perspective view of the clamp according to the invention,

FIG. 2 is a cross-section on a larger scale along line 2—2 of FIG. 1.

FIG. 3 is a front view of the clamp,

DETAILED DESCRIPTION OF THE PREFERRED EMBODIMENTS

Figure 3A:
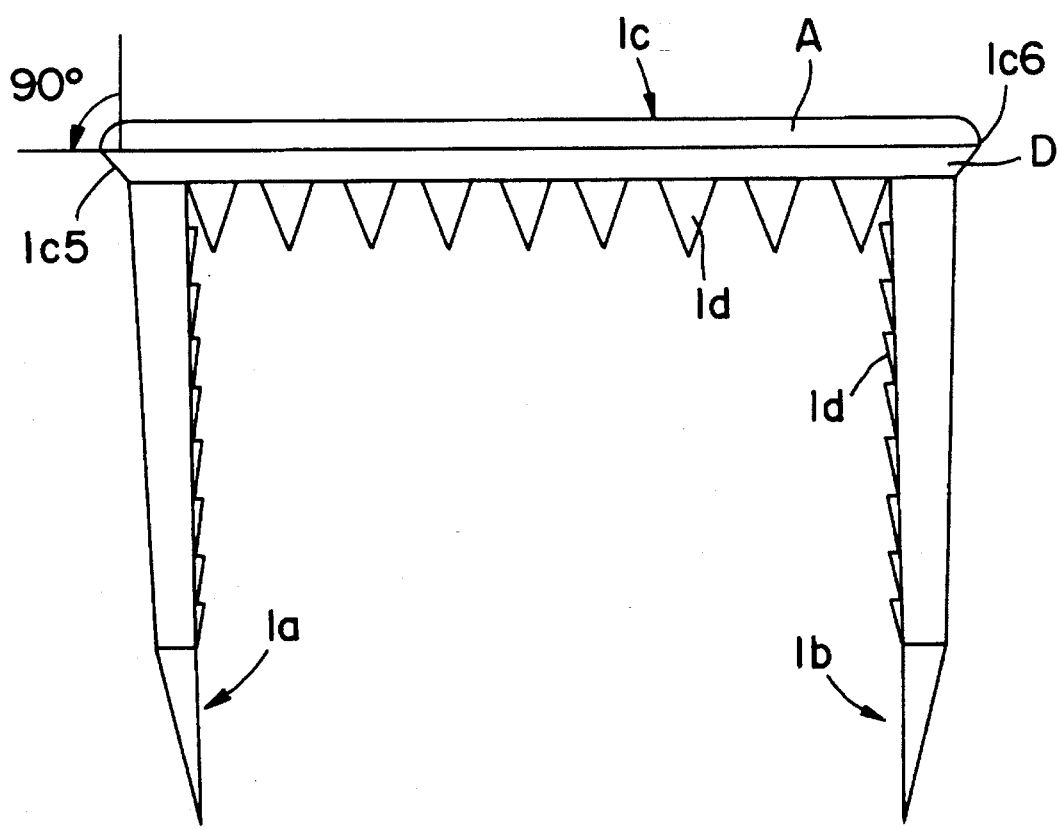
FIG. 3a is a front view of an alternate embodiment of the clamp having serrations on the leg insides and bottom of the yoke.

It is recalled at this stage that the surgical clamp designated in full as (1) consists of two parallel anchoring legs (1a and 1b) joined perpendicularly by a rectilinear part (1c) or yoke. The clamp, therefore, has the form of an inverted-U. The ends of the legs (1a and 1b) are beveled to points to facilitate penetration into cortical bone substance. The width (1) of the yoke (1c) is greater than the cross-sectional width of the legs (1a and 1b). These characteristics will not be described in detail as they are common knowledge among those skilled in the art. Likewise, leg insides and outside (1a and 1b) and the bottom of the yoke (1c) may be serrated (1d) so as to secure the clamp to the bone.

According to a basic feature of the invention, the yoke (1c) has a flat section and two of its edges (1c1–1c2) and two short edges 1c5–1c6). The edges are linked to the flat top (1c3) by a generously rounded profile (A). The edges are linked to the bottom (1c4) by an inclined flank (D) (FIG. 2). The rounded profile (A) is constituted by an arc of a circle subtending substantially 90° at the center. The inclined flanks (D) are shaped directly in line with the rounded edges (A). The inclined flanks (D) are linked to the vertical plane defined by the legs (1a and 1b) at an obtuse angle ($\alpha$).

The transition area between the rounded profile (A) of the edges (1c1–1c2 and 1c5–1c6) and the inclined flank (D) is located roughly in the middle of the height of the yoke (1c).

Figure 4:
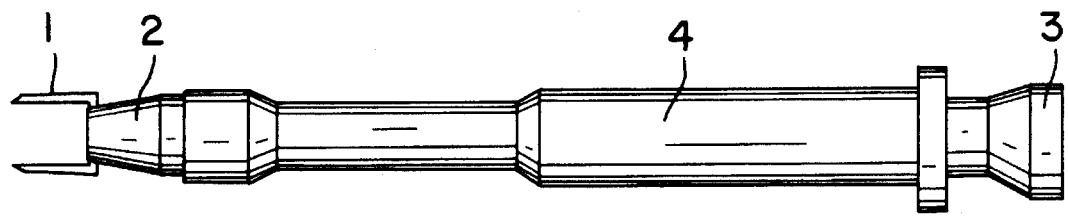
FIG. 4 is a front view of the clamp inserted into a driving device.
Figure 5:
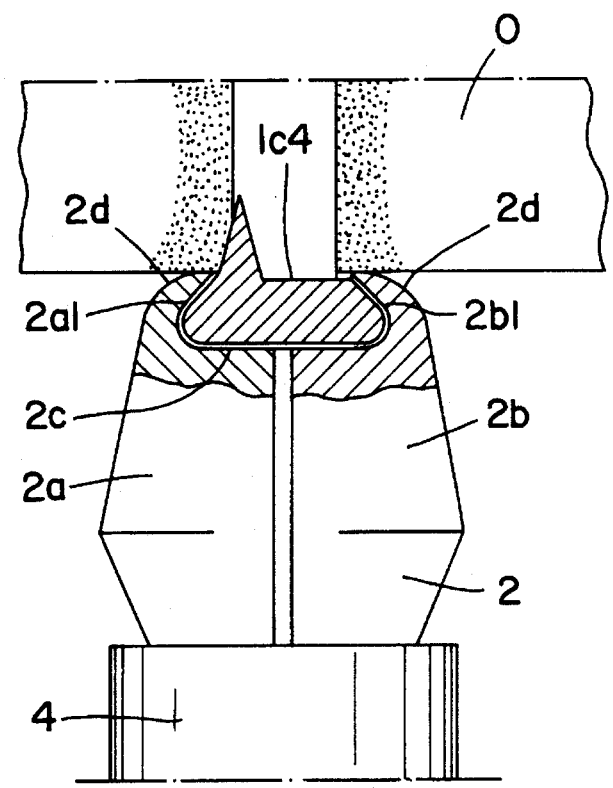
FIG. 5 is a cross-section on a larger scale, showing the clamp loaded into the driving device and driven home.

The cross-section of the yoke (1c) thus defined is designed to mate with the moving pans of any type of known and appropriate driving device. As shown in FIGS. 4 and 5, the moving part (2) is two jaws (2a–2b) acting as pincers that are controlled by an actuator (3) located at the end of a handle (4).

According to the invention, each of the jaw insides is recessed (2a1–2b1) to closely fit the cross-section of the yoke (1c). From the tip inwards, each of these recessed jaws notably features an inclined flank transiting through a large radius of curvature of the same value as the rounded profiles (A) down to the bottom part (2c) designed to accommodate the top of the clamp (1c3).

Due to the inclined mating flanks of the jaw insides and the yoke flanks (D), the clamp is locked in place with no opportunity for angular movement at the moment of impact.

According to a further aspect and as shown in the FIG. 5, the jaw tips (2) are curved inwards on the outside (2d), allowing them to be held in a position tangential to the bone surface (O). These features permit the clamp to be driving home with the bottom of the yoke (1c4) touching the bone.

Hence, no asperities appear when the clamp is driven home. The generously rounded profile (A) prevent lesions from occurring when the clamp touches the skin.

The advantages are obvious from the description.

I claim:

1. A surgical clamp comprising two parallel anchoring legs coupled to a yoke suitable for insertion into a driving device the yoke having a flat top, a bottom, a middle height, two long edges and two short edges, the edges being coupled to the flat top by a round profile and the bottom by an inclined flank forming an obtuse angle $\alpha$ with respect to the vertical plane, the round profile being made up of an arc of a circle with a central angle of substantially 90°, the inclined flank being shaped directly in line with the round profile, a transition area between the round profile and the inclined flank is located roughly in the middle of the height of the yoke.

2. The surgical clamp according to claim 1 wherein at least one of the two parallel anchoring legs has an inside having serrations thereon.

3. The surgical clamp according to claim 1 wherein at least one of the two parallel anchoring legs has an outside having serrations thereon.

4. The surgical clamp according to claim 1 wherein the bottom of the yoke is serrated.

* * * * *